United States Patent [19]

Paust et al.

[11] Patent Number: 4,918,191
[45] Date of Patent: Apr. 17, 1990

[54] PREPARATION OF 2-N-PROPYL-4-AMINO-5-METHOXYMETHYL-PYRIMIDINE

[75] Inventors: Joachim Paust, Neuhofen; Hansgeorge Ernst, Speyer, both of Fed. Rep. of Germany

[73] Assignee: BASF Aktinegesellschaft, Ludwigshafen, Fed. Rep. of Germany

[21] Appl. No.: 393,976

[22] Filed: Aug. 15, 1989

[30] Foreign Application Priority Data

Sep. 2, 1988 [DE] Fed. Rep. of Germany ....... 3829850

[51] Int. Cl.4 .......................................... C07D 239/42
[52] U.S. Cl. .................................................. 544/326
[58] Field of Search ........................................ 544/326

[56] References Cited
FOREIGN PATENT DOCUMENTS 1276663 10/1961 France .
953876 4/1964 United Kingdom .

Primary Examiner—John M. Ford
Attorney, Agent, or Firm—John H. Shurtleff

[57] ABSTRACT

In an improved process for the preparation of 2-n-propyl-4-amino-5-methoxymethyl-pyrimidine of the formula I

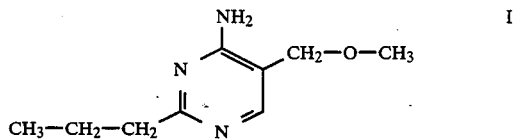

by reacting butyramidine II

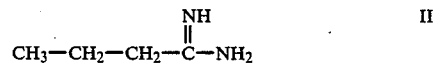

with α-methoxymethyl-β-methoxyacrylonitrile III

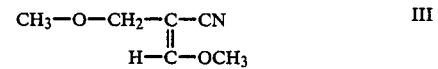

the butyramidine II is reacted with a 0.4–5 molar excess of α-methoxymethyl-β-methoxyacrylonitrile III at from −10° to +20° C.

4 Claims, No Drawings

PREPARATION OF 2-N-PROPYL-4-AMINO-5-METHOXYMETHYL-PYRIMIDINE

The present invention relates to an improved process for the preparation of 2-n-propyl-4-amino-5-methoxymethylpyrimidine of the formula I

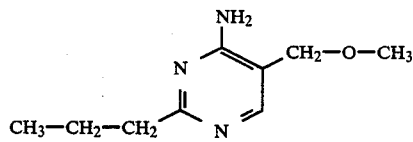

by reacting butyramidine II

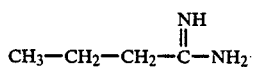

with α-methoxymethyl-β-methoxyacrylonitrile III

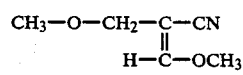

2-n-Propyl-4-amino-5-methoxymethylpyrimidine I is the direct intermediate for the coccidiostatic agent amprolium, which is used in veterinary medicine and can be prepared from I, for example according to French Patent 1,276,663.

The preparation of I is described in French Patent 1,276,663 and British Patent 953,876. According to their virtually identical procedures, the butyramidine II liberated in situ from butyramidine hydrochloride with sodium methylate is reacted with equimolar amounts of α-methoxymethyl-β-methoxyacrylonitrile in boiling methanol to give I. Isolation of the desired product I from the reaction mixture requires the following measures:

Removal of methanol by distillation
Treatment of the residue with 50% strength aqueous sodium hydroxide solution at elevated temperatures
Extraction of this mixture with chloroform
Evaporation of the chloroform solution
Dissolution of the residue in xylene
Concentration of the xylene solution
Crystallization with cooling.

According to British Patent 953,876, this process gives I in only a moderate yield of 75.1%. In the French Patent, the yield of I is not stated. Neither the French Patent nor the British Patent contain the physical data of product I or information about its purity.

Apart from the disadvantage of a moderate yield, the processes described entail high costs in terms of apparatuses and energy owing to the multistage working-up procedure, and the use of three solvents, methanol, chloroform and xylene, entail further costs.

It is an object of the present invention to provide a process which permits the preparation of I in good yields and in high purity and is economical and does not have the disadvantages of the known processes.

We have found that this object is achieved by a process for the preparation of 2-n-propyl-4-amino-5-methoxymethylpyrimidine of the formula I

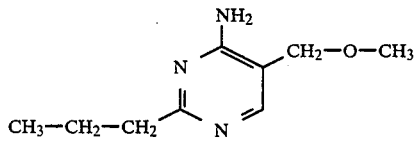

by reacting butyramidine II

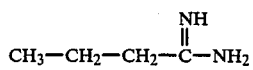

with α-methoxymethyl-β-methoxyacrylonitrile III

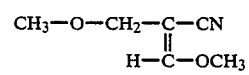

wherein the butyramidine II is reacted with a 0.4–5 molar excess of α-methoxymethyl-β-methoxyacrylonitrile III at from −10° to +20° C.

The reaction of the butyramidine II with α-methoxymethyl-β-methoxyacrylonitrile takes place in accordance with equation (1)

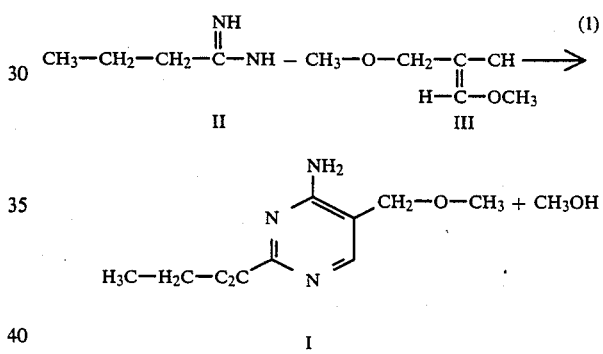

one mole of methanol being formed per mole of III converted.

The molar excess of compound III over the butyramidine II is advantageously from 0.4 to 1.5, preferably from 0.8 to 1.2, moles. The use of a larger excess of III, for example a 5-molar excess, is possible but leads to no significant improvement in the result of the process. The reaction is carried out at low temperatures, in general from −10° to +20° C., advantageously from −5° to 15° C., in particular from 0° to 10° C.

In the novel process, the formation of undesirable byproducts which can be separated off neither by distillation nor by crystallization is suppressed. The pyrimidine I is thus formed in a high purity of >99% and can be isolated from the reaction mixture without further working-up, for example by crystallization or distillation. The yield achievable in the novel process is greater than 90% of theory.

In carrying out the process, the various procedures may be adopted, and the choice as to which of the possible procedures stated below is used depends in general on the operational conditions, for example on the availability of appropriate apparatuses.

If the desired product I is to be isolated by crystallization from the reaction mixture, it is advantageous to use the butyramidine II in a form which is substantially or, advantageously, completely free of accompanying salt-like substances.

Butyramidine of such quality can, for example, be produced in a separate stage from butyramidine hydrochloride, the commercial and stored form of butyramidine, by reaction with a strong, nonaqueous base, the corresponding salts being obtained as insoluble precipitates. The base can be used in stoichiometric amounts or in an amount slightly less than the stoichiometric amount. Because it is economically available, sodium methylate in the form of its commercial, 30% strength methanolic solution is advantageously used as the base. However, it is also possible to use other bases, such as sodium ethylate, potassium tert-butylate or potassium amide. The methanol may likewise be replaced by other solvents or by solvent mixtures. Advantageously, solvents which are inert under the reaction conditions for the preparation of pyrimidine I are chosen for this purpose, for example ethanol, isopropanol, tetrahydrofuran or dioxane; otherwise, the solvents should be substantially separated off before the butyramidine is used in the novel process.

The amount of solvent required in the preparation of the free butyramidine II is determined by the desired viscosity of the butyramidine solution, and this depends in turn on the particular apparatuses and processes, for example filtration or centrifuging, which are used for separating off the salts suspended in the butyramidine solution.

Butyramidine solutions obtained in this manner are advantageously concentrated before being used in the reaction, so that their solvent content is in general from 10 to 20% by weight. Usually, the concentration is carried out under reduced pressure and at from 20° to 40° C. It is also possible completely to remove the solvent from the butyramidine solution, but this does not in general have any further advantages.

The butyramidine II obtained in this manner is used in the reaction. For this purpose, the butyramidine is advantageously metered into the $\alpha$-methoxymethyl-$\beta$-methoxyacrylonitrile III initially taken in the reaction vessel. The reaction may be carried out in the presence of an additional solvent, but this does not as a rule have any further advantages, since the excess III present in the reaction vessel and the methanol formed in the course of the reaction act as solvents and ensure that the reaction mixture is stirrable.

The pyrimidine I formed is precipitated during the reaction itself and can be separated off from the mother liquor at the end of the reaction, for example by filtration or centrifuging. The desired product I is obtained in such high purity that it need virtually only be washed with a suitable solvent, for example methyl tert-butyl ether (MTB) to remove adhering III.

The use of the mother liquor, combined with the wash liquid, as a solvent for further reactions (1) has proven a particularly advantageous procedure.

For this purpose, the mother liquor, which still contains considerable amounts of the product I in addition to the excess starting material III, is substantially freed from methanol and MTB, in general at from 20° to 30° C. and under reduced pressure. The consumed $\alpha$-methoxy-methyl-$\beta$-methoxyacrylonitrile III is then replenished, and the butyramidine II is then again added to this mixture in the manner described, this being done, as described, in amounts such that the molar excess of III over II is 0.4 to 1.5. The reaction is then carried out, as described, at from $-10°$ to 20° C., after which the resulting product I is separated off in a similar manner. This process can be repeated virtually as often as desired.

If it is preferred to isolate the pyrimidine I from the reaction mixture by distillation, the reaction can be carried out as described above, with regard to the reaction procedure and the form in which the butyramidine is used. However, it may also be advantageous to liberate the butyramidine II from its hydrochloride in situ, ie. in the presence of initially taken III in the reaction vessel, and the base used may be the same as that used for the separate liberation of butyramidine II.

In an advantageous procedure, the butyramidine hydrochloride in excess III is initially taken and a solution of the base, for example 30% strength methanolic sodium methylate solution, is added dropwise to this suspension at from $-10°$ to 20° C. The salts precipitated in the course of the butyramidine liberation are advantageously separated off in a conventional manner after the end of the reaction and before distillation of the reaction mixture. Of course, in this embodiment the solvent is added to the reaction mixture in an amount sufficient to prevent the pyrimidine I formed in the course of the reaction from crystallizing out, since otherwise the desired product I will be separated off together with the salts.

The distillation of the reaction mixture is carried out in a conventional manner by first removing the solvent by distillation, under atmospheric or reduced pressure, and then subjecting the remaining, sparingly volatile residue, which in addition to the product I also contains the excess starting compound III, to fractional distillation under reduced pressure.

In the novel process, the reaction vessels need not meet any special requirements. In general, simple stirred kettles which are provided with a cooling apparatus are used.

The starting materials used and the methods for their preparation are known (cf. for example French Patent 1,276,663) or can be bought. $\alpha$-Methoxymethyl-$\beta$-methoxyacrylonitrile can be used as a mixture of its E and Z isomers.

EXAMPLES

Example 1

12.96 g (0.105 mole) of butyramidine hydrochloride were suspended in 50 ml of methanol, and 18.0 g of a 30% strength solution of sodium methylate (0.10 mole) in methanol were added at from 2° to 5° C. The precipitated sodium chloride was filtered off and washed with 5 ml of methanol. The filtrate was evaporated down in a rotary evaporator at a bath temperature of 30° C. and under 5 mbar.

The crude butyramidine II thus obtained (methanol content about 10% by weight) was added dropwise to 25.4 g (0.2 mole) of E,Z-$\alpha$-methoxymethyl-$\beta$-methoxyacrylonitrile III in the course of 15 minutes at from 2° to 5° C. Stirring was carried out for 6 hours at 5° C., some of the desired product I crystallizing out. The crystalline product was filtered off under reduced pressure and the crystals were washed with a little MTB. Yield: 8.88 g (38% of theory).

The mother liquor was substantially freed from methanol and MTB at a bath temperature of 30° C. and under 5 mbar and, after replenishment with 12.7 g (0.1 mole) of III, 0.1 mole of II was added, as described above. Stirring was continued for 10 hours at from 2° to 5° C.

The precipitated crystals were isolated in the manner described. Yield: 15.85 g (87.6% of theory); melting point: 67°–70° C.

5 further reactions by the procedure described above, ie. with reuse of the mother liquor, gave an average yield of I of 91.6% of theory.

Example 2

12.35 g (0.1 mole) of butyramidine hydrochloride were suspended in 27.23 g (0.2 mole) of III, and 18 g of a 30% strength solution of sodium methylate (0.1 mole) in methanol were added dropwise at from 2° to 5° C. in the course of 15 minutes. Stirring was carried out for 10 hours at 10° C., after which the precipitated sodium chloride was filtered off. The methanol was distilled off in a rotary evaporator. The residue was subjected to fractional distillation under reduced pressure. 11.56 g (0.091 mole) of III of boiling point 75°–81° C./0.5 mbar and 16.11 g (89% of theory) of I of boiling point 104°–107° C./0.4 mbar were obtained.

We claim:

1. A process for the preparation of 2-n-propyl-4-amino-5-methoxymethylpyrimidine of the formula I

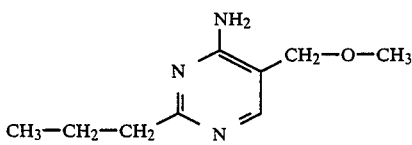

by reacting butyramidine II

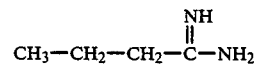

with α-methoxymethyl-β-methoxyacrylonitrile III

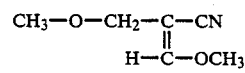

wherein the butyramidine II is reacted with a 0.4–5 molar excess of α-methoxymethyl-β-methoxyacrylonitrile III at from −10° to +20° C.

2. A process as claimed in claim 1, wherein the butyramidine II is used in a form which is substantially free of accompanying salt-like substances.

3. A process as claimed in claim 1, wherein the butyramidine II is used in the form which is substantially free of accompanying salt-like substances, and the product I obtained from its reaction with α-methoxymethyl-β-methoxyacrylonitrile is crystallized from the reaction mixture, the crystals are separated off and the mother liquor is used as a solvent for further reactions II with III.

4. A process as claimed in claim 1, wherein the product 2-n-propyl-4-amino-5-methoxymethylpyrimidine I is isolated from the reaction mixture by distillation.

* * * * *